United States Patent
Schmolke et al.

(10) Patent No.: US 6,333,785 B1
(45) Date of Patent: Dec. 25, 2001

(54) STANDARD FOR CALIBRATING AND CHECKING A SURFACE INSPECTION DEVICE AND METHOD FOR THE PRODUCTION THEREOF

(75) Inventors: Rüdiger Schmolke; Dieter Gräf, both of Burghausen; Robert Kerschreiter, Kirchdorf; Hans-Adolf Gerber, Burghausen; Anton Luger, Wittibreut, all of (DE); Monique Suhren, Portland, OR (US)

(73) Assignee: Wacker Siltronic Gesellschaft für Halbleitermaterialien AG, Burghausen (DE)

( * ) Notice: Subject to any disclaimer, the term of this patent is extended or adjusted under 35 U.S.C. 154(b) by 0 days.

(21) Appl. No.: 09/380,329
(22) PCT Filed: Mar. 6, 1998
(86) PCT No.: PCT/EP98/01313
§ 371 Date: Nov. 12, 1999
§ 102(e) Date: Nov. 12, 1999
(87) PCT Pub. No.: WO98/39638
PCT Pub. Date: Sep. 11, 1998

(30) Foreign Application Priority Data

Mar. 6, 1997 (DE) .............................. 197 09 255

(51) Int. Cl.[7] ..................................................... G01J 1/10
(52) U.S. Cl. ..................................................... 356/243.4
(58) Field of Search ...................... 352/243.1, 243.2, 352/243.3, 243.4, 243.5, 237.1, 237.2, 237.3, 237.4, 237.5

(56) References Cited

U.S. PATENT DOCUMENTS

| | | | |
|---|---|---|---|
| 4,386,850 | * 6/1983 | Leahy | 356/243 |
| 5,383,018 | 1/1995 | Sadjadi . | |
| 5,599,464 | 2/1997 | Laind et al. . | |
| 6,130,016 | * 10/2000 | Kent | 430/30 |

FOREIGN PATENT DOCUMENTS

| | | |
|---|---|---|
| 0 180 756 | 5/1986 | (EP) . |
| WO92/07248 | 4/1992 | (WO) . |

OTHER PUBLICATIONS

Patent Abstracts of Japan, vol. 018, No. 399 (P–1776) Jul, 26, 1994 & JP 06 117845 A (Advantest (Corp.), Apr. 28, 1994.

* cited by examiner

*Primary Examiner*—Hoa Q. Pham
(74) *Attorney, Agent, or Firm*—Collard & Roe, P.C.

(57) ABSTRACT

The invention relates to a reproducible standard for calibrating and checking the bright-field channel of a surface inspection device used for examining the flat surface of a sample and to a method for producing said standard whereby a microstructure is produced on a surface of a substrate provided as a standard, characterized in that the microstructure is smoothed out.

5 Claims, 2 Drawing Sheets

STANDARD FOR CALIBRATING AND CHECKING A SURFACE INSPECTION DEVICE AND METHOD FOR THE PRODUCTION THEREOF

BACKGROUND OF THE INVENTION

1. Field of the Invention

The invention relates to a reproducible standard for calibrating and checking the bright field channel of a surface inspection device which is used for examinations of a smooth surface of a specimen. The invention also relates to a method for making the standard

2. The Prior Art

Smooth surfaces of a specimen, for example the sides of semiconductor wafers, are customarily examined using surface inspection devices, the surface to be examined being automatically scanned using a laser beam. Defects on the surface of the specimen, in particular raised and lowered portions of materials, and also foreign particles, can be identified and quantified by detecting and evaluating the light scattered by the surface of the specimen. For measurements in the dark field channel of the surface inspection device, that is to say for measurements of the scattered light produced non-specularly when the laser beam strikes, internationally recognized standards are available, using which the dark field channel of the surface inspection device can be calibrated and checked. Such a standard consists, for example, of a polished semiconductor wafer, on one of whose sides a particular number of microspheres with particular average size and size distribution are deposited.

The microspheres represent only a rough approximation of the defects which are actually to be found on smooth surfaces. Furthermore, especially defects which, over a comparatively large lateral extent, span only small height differences, are not detected in the dark field channel. They can, however, be picked up in the bright field channel of the surface inspection device, that is to say by measuring the laser light reflected specularly from the surface of the specimen. They are picked up customarily by measuring intensity losses of the laser beam reflected in the specular direction or by measuring the differential interference contrast ("Normaski contrast"). However, there is currently no reliable standard with which the bright field channel of the surface inspection device can be checked and calibrated. Standards which are based on substrates that have microspheres applied to them are found to be unsatisfactory for examinations in the bright field channel. A bright field standard of this kind must have comparatively large microspheres applied to it. Since the adhesion of microspheres to a substrate decreases as the sphere diameter increases, it is difficult to work with the standard. Furthermore, such a standard is not cleanable. It has also been found inappropriate to use known step-height standards as standards for measurements in the bright field channel. This is because, when such standards are used, no evidence of edge gradients of defects is encountered, so that realistic defect characterization is not possible.

SUMMARY OF THE INVENTION

The present invention achieves the object of providing a standard which is suitable for calibrating and checking the bright field channel of a surface inspection device.

The invention relates to a reproducible standard for calibrating and checking the bright field channel of a surface inspection device which is used for examinations of a smooth surface of a specimen, and to a method for making the standard, a microstructure being produced on a surface of a substrate provided as a standard, which is characterized in that the microstructure undergoes a smoothing treatment.

The standard is distinguished, in particular, in that defects found on the smooth surface of a specimen which are detectable in the bright field channel are realistically replicated by microstructures applied to the standard. The standard can therefore also advantageously be used for statistical process control (SPC) purposes. Furthermore, the standard can be reproduced with high accuracy. The bright field channel signal that can be detected when carrying out measurement on the standard can be directly attributed to a specific defect geometry. The standard can moreover be cleaned without problem. Lastly, with the aid of the standard, it is also possible to establish differences in sensitivity of the bright field channel with respect to a surface to be tested.

In order to make the standard, a substrate is needed which has at least one planar surface on which a microstructure can be formed. Preferred substrates are semiconductor wafers, in particular monocrystalline semiconductor wafers of silicon, which have at least one prepolished or mirror-polished side. These semiconductor wafers may also be coated, for example with an oxide layer, a nitride layer or with an epitaxial layer. In a first step of the method, the planar surface of the substrate, or a part of this surface, is structured. Microstructures are produced on the surface using methods which are known per se. Particularly preferred methods are lithographic methods, for example photolithography, ion beam. (focussed ion beam) lithography and electron beam lithography, as well as structuring methods using etching (micromachining) and plasma etching. Of course, combinations of the said methods may also be used for structuring the surface of the substrate.

Preferred microstructures are patterns of regularly repeating geometrical objects, the extent of an object being preferably from 1 $\mu$m 400 $\mu$m in width and lengths and from 1 nm to 1 $\mu$m in height. The object may be formed as raised or lowered parts, which protrude from the substrate plane and cut into the substrate, respectively. Examples of such objects include columnar raised or lowered parts. In contrast to microspheres deposited on the substrate surface, the objects form an integral unit with the substrate.

In principle, signals in the bright field channel of a surface inspection device can be recorded just with substrates structured in this way. However, the geometry of the objects still differs substantially from the geometry of the defects which are customarily found on the specimens to be examined. In particular, such objects have high edge gradients. In order to obtain a reliable standard for calibrating and checking the bright field channel, it is therefore proposed to carry out a smoothing treatment on the structured surface of the substrate. By such a treatment, in particular, edges are removed and the objects are altered in such a way that their appearance is modelled on that of the defects to be found on the surface of specimens.

The smoothing treatment is preferably carried out by polishing, plasma etching, etching with a non-preferential. etch or by a combination of the said methods.

The bright field channel of a surface inspection device is regularly calibrated and checked using standards made in the described way. Defects, which are detectable in the bright field channel, on smooth surfaces of specimens can then be quantitatively determined using the surface inspection device in automatically performed serial examinations, and assigned in terms of appearance and size to a particular type of defect.

Specimens for automatic serial examinations are, in particular, semiconductor wafers, for, example monocrystalline silicon wafers, coated semiconductor wafers, optical displays (flat panel displays) as well as electronic and optical storage media (discs, compact discs, hard disks).

DETAILED DESCRIPTION OF PREFERRED EMBODIMENTS

Figure 1A:
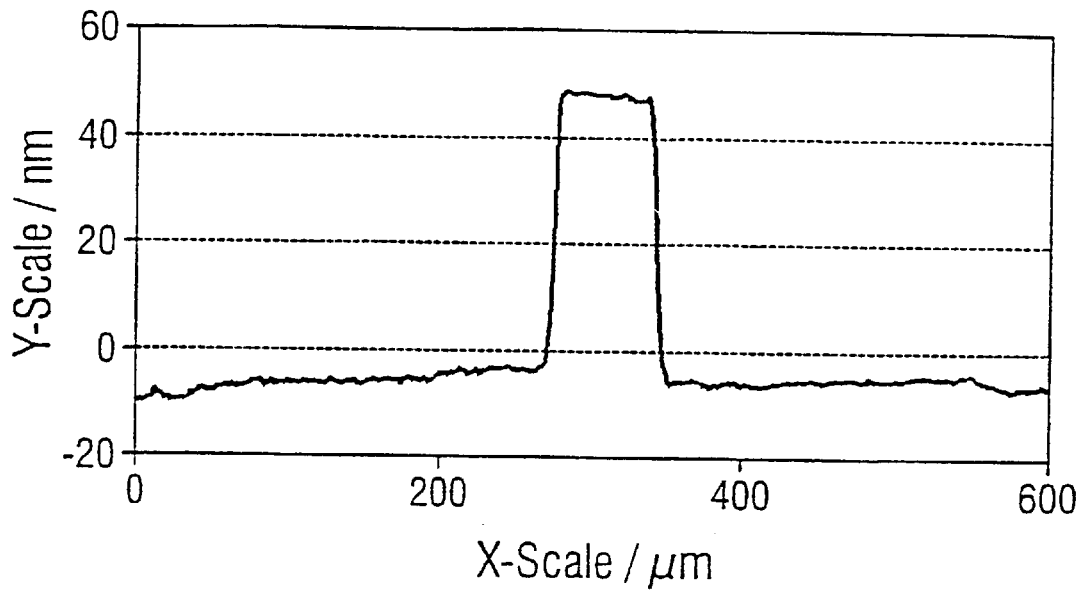
FIG. 1a shows a representation of an object of a microstructure produced on a substrate.
Figure 1B:
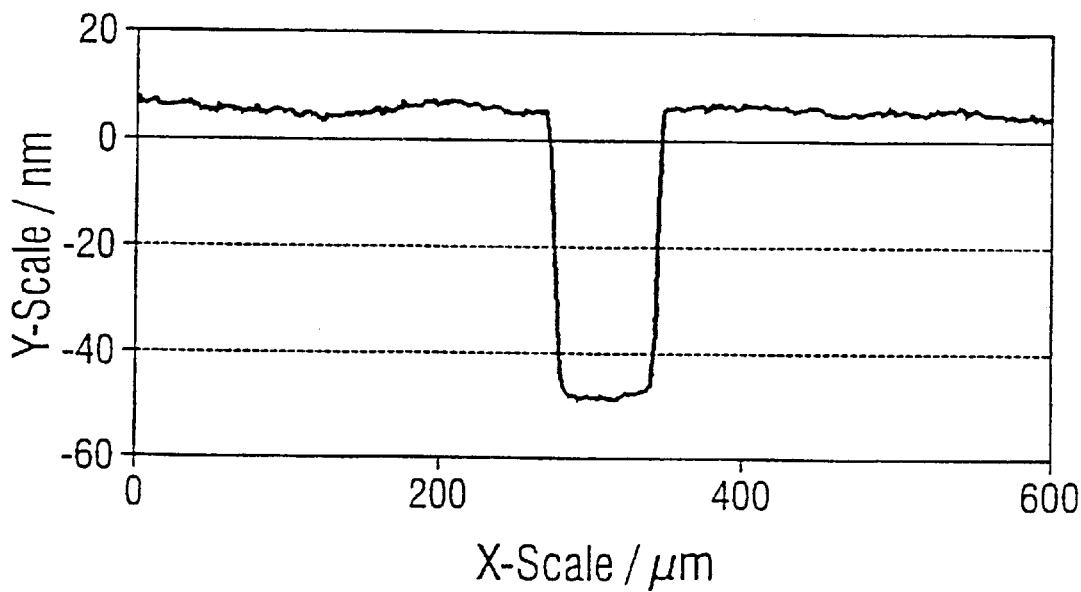
FIG. 1b shows a representation of an object of a microstructure produced on a substrate.
Figure 2A:
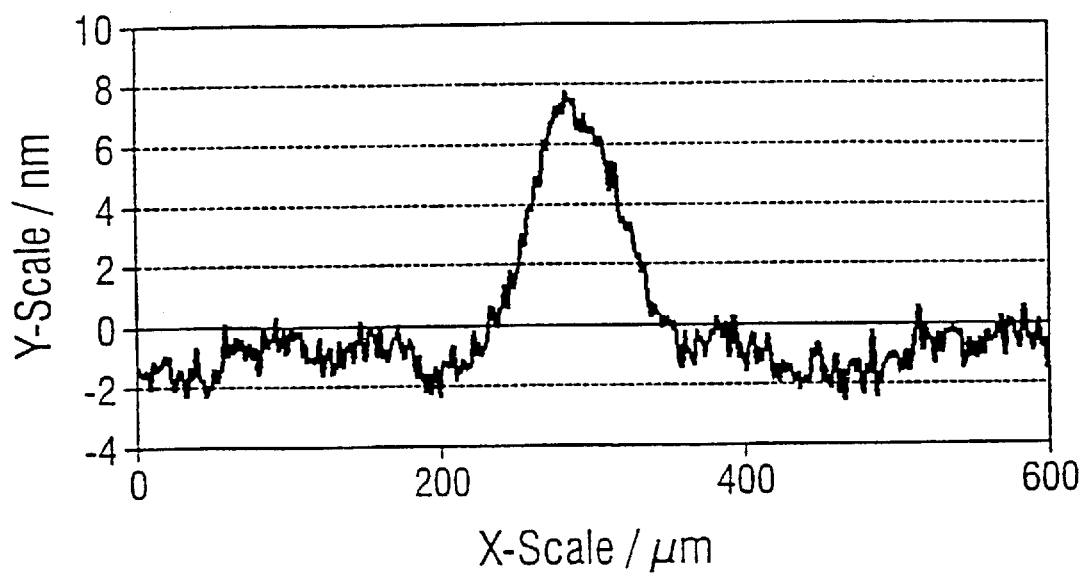
FIG. 2a shows how the appearance of the object has changed after a polishing step.
Figure 2B:
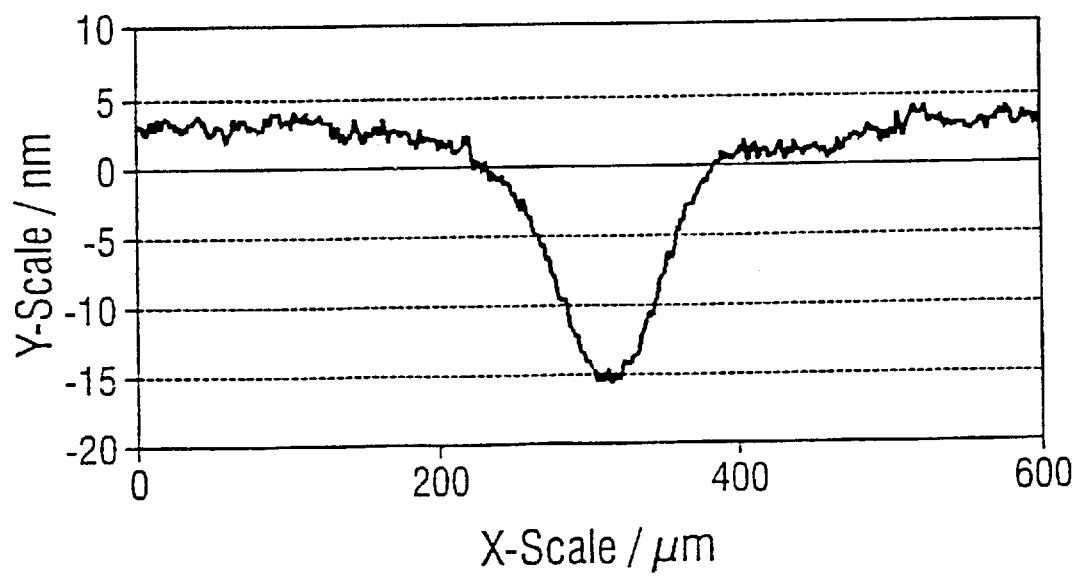
FIG. 2b shows how the appearance of the object has changed after a polishing step.

The invention will be explained in more detail below with reference to a preferred illustrative embodiment and with reference to figures. The illustrative embodiment relates to making a standard which, in particular, is suitable for calibrating the bright field channel of surface inspection devices that are intended for serial examinations of silicon wafers. FIGS. 1a and 1b each show a representation of an object of a microstructure produced on a substrate. FIGS. 2a and 2b represent how the appearance of the objects has changed after a polishing step. The figures show local cross sections through the semiconductor wafer, which were produced when observing the objects with the aid of an interference microscope.

To make the bright field channel standard, two polished semiconductor wafers of silicon having a diameter of 200 mm were chosen as substrates (wafer a and wafer b). The surfaces of one side of each of the semiconductor wafers consisted of a 25 nm thick oxide layer produced by a heat treatment. This layer was photolithographically structured. The microstructure produced comprised a pattern of regularly arranged cylindrical oxide columns having a diameter of about 100 $\mu$m (wafer a) or columnar lowered parts in the oxide layer (layer b), respectively.

The substrate wafers structured in this way were in principle already suitable as a bright field channel standard. When it was examined in the bright field channel of a surface inspection device, signals were obtained whose distribution lay around a central value, this value being correlated with the oxide layer thickness. Since, however, the microstructures which had been produced did not realistically enough model the usual defects which are to be found, for example, on polished, or epitaxially coated silicon wafers, these microstructures were copied over into the silicon wafers and smoothed. The wafers were treated with an 85° C. hot alkalinically oxidizing etch solution of the so-called SC1 type (with an $NH_4OH:H_2O_2:H_2O$ ratio of 1:1:5), which is capable of eroding the oxide and the silicon at rates in the ratio 1:2. The oxide layer was fully removed by the etching treatment. Because of the different erosion rates, this created about 50 nm high silicon columns, (layer a), one of which is illustrated in FIG. 1a, and columnar lowered parts (wafer b), one of which is illustrated in FIG. 1b, respectively.

The structured sides of the two substrate wafers were then polished with two 2 $\mu$m erosion in the conventional way. FIGS. 2a and 2b clearly show that the contours of the objects have been substantially smoothed by the polishing. The objects are therefore modelled on the defects to be found on specimens, because their contours likewise have scarcely any edges. An examination of the standards which had been made in the bright field channel of a surface inspection device gave a narrow signal distribution around a central value, which reflected the geometrical dimensions of the object. By suitable variation of the polishing process, in particular by altering the polishing erosion, the vertical dimensions of the microstructures can be modified.

What is claimed is:

1. Method for making a reproducible standard for calibrating and checking a bright field channel of a surface inspection device which is used for examination of a smooth surface of a specimen comprising the steps of producing a microstructure of objects on a surface of a substrate provided as a standard; and said objects having edges and having an appearance; and causing the microstructure to undergo a smoothing treatment; and by said smoothing treatment, said edges are removed and the objects are altered so that said appearance is modeled on that of defects to be found on the surface of the specimen.

2. Method according to claim 1, wherein the microstructure is produced using a method which is selected from the group consisting of a lithographic method, photolithography, ion beam lithography, focused ion beam lithography, electron beam lithography, etching, micromachining, plasma etching, and any combination of these methods.

3. Method according to claim 1, wherein the smoothing treatment is selected from the group consisting of polishing, plasma etching, etching with a non-preferential etch, and any combination thereof.

4. Method according to claim 1, wherein the substrate is selected from the group consisting of a semiconductor wafer, a monocrystalline semiconductor wafer of silicon which has at least one prepolished side or mirror-polished side, and a coated semiconductor wafer having a coating selected from the group consisting of an oxide layer, a nitride layer, and an epitaxial layer.

5. Reproducible standard for calibrating and checking the bright field channel of a surface inspection device which is used for examination of a smooth surface of a specimen, produced by a method according to claim 1.

* * * * *